(12) United States Patent
DeLonzor

(10) Patent No.: US 7,976,538 B2
(45) Date of Patent: Jul. 12, 2011

(54) FAST FIBROADENOMA TREATMENT SYSTEM AND METHOD

(75) Inventor: Russell L. DeLonzor, Pleasanton, CA (US)

(73) Assignee: Sanarus Technologies, LLC, Pleasanton, CA (US)

( * ) Notice: Subject to any disclaimer, the term of this patent is extended or adjusted under 35 U.S.C. 154(b) by 1091 days.

(21) Appl. No.: 11/736,001

(22) Filed: Apr. 16, 2007

(65) Prior Publication Data

US 2008/0255552 A1    Oct. 16, 2008

(51) Int. Cl.
*A61B 18/02* (2006.01)

(52) U.S. Cl. .................................................. 606/23

(58) Field of Classification Search ............... 606/20–26
See application file for complete search history.

(56) References Cited

U.S. PATENT DOCUMENTS

| | | | |
|---|---|---|---|
| 4,566,291 A | 1/1986 | Halavais | |
| 5,207,674 A * | 5/1993 | Hamilton | 606/20 |
| 5,800,488 A * | 9/1998 | Crockett | 607/105 |
| 5,946,920 A | 9/1999 | Clarke | |
| 2002/0016540 A1 * | 2/2002 | Mikus et al. | 600/407 |
| 2004/0082943 A1 * | 4/2004 | Littrup et al. | 606/21 |
| 2004/0207252 A1 | 10/2004 | Woll | |
| 2005/0123425 A1 | 6/2005 | Smith et al. | |
| 2006/0155267 A1 * | 7/2006 | Berzak et al. | 606/20 |
| 2006/0235375 A1 | 10/2006 | Littrup et al. | |
| 2010/0179527 A1 * | 7/2010 | Watson et al. | 606/21 |

OTHER PUBLICATIONS

Littrup et al., Cryotherapy for Breast Fibroadenomas, Jan. 2005, Radiology, vol. 234, 63-72.*

* cited by examiner

*Primary Examiner* — Roy D Gibson
*Assistant Examiner* — Benjamin Lee
(74) *Attorney, Agent, or Firm* — K. David Crockett, Esq.; Niky Economy Syrengelas, Esq.; Crockett & Crockett, PC

(57) ABSTRACT

A method of treating fibroadenomas with optimized freezing periods at a single freezing temperature and minimal thawing time between freezing periods, and a system for accomplishing the method.

20 Claims, 5 Drawing Sheets

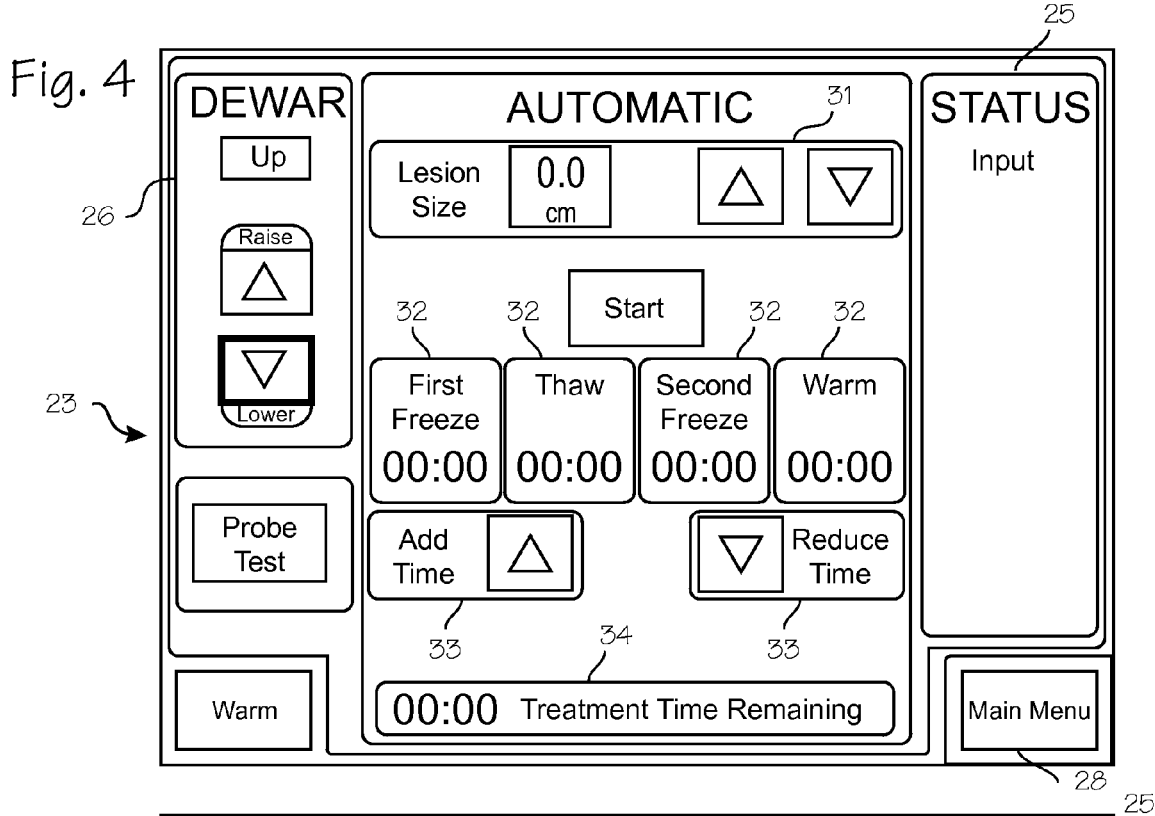
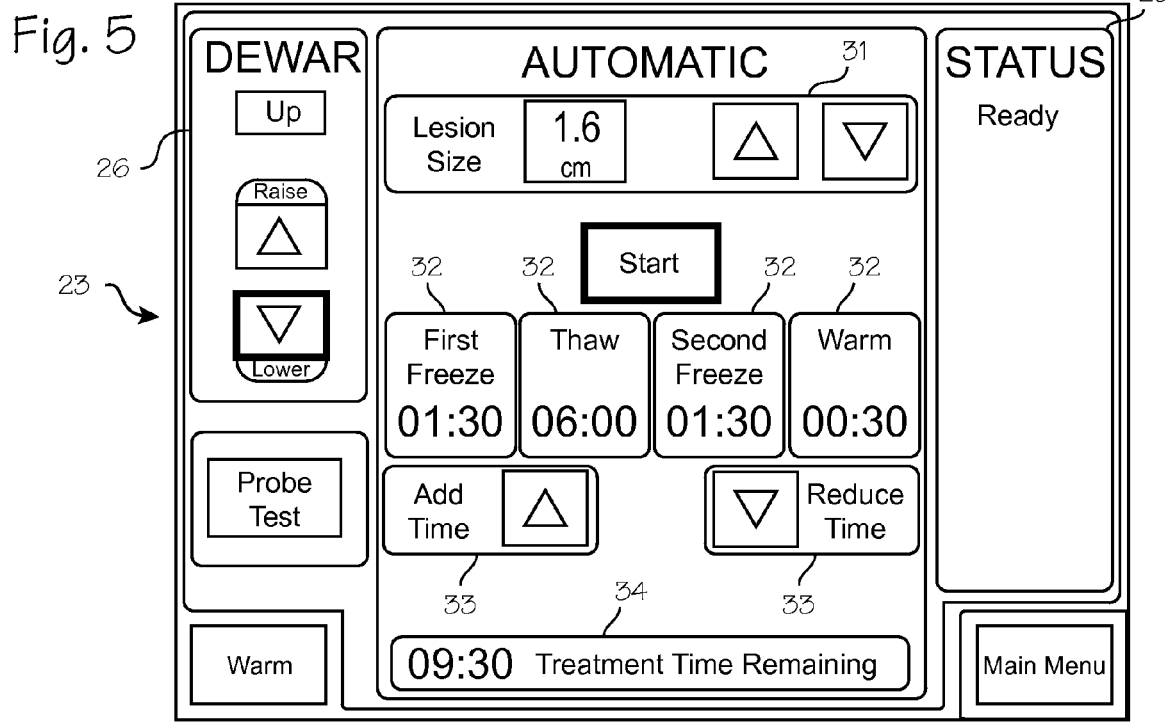

FAST FIBROADENOMA TREATMENT SYSTEM AND METHOD

FIELD OF THE INVENTIONS

The inventions described below relate the fields of cryosurgery and cryosurgical treatment of breast lesions.

BACKGROUND OF THE INVENTIONS

The methods and systems described below provide for optimal treatment of fibroadenomas. A fibroadenoma is a benign tumor found in women's breasts. They are small, solid, round, rubbery masses that are typically found in breast self-exams or mammography. Fibroadenomas are harmless, but may be painful, palpable and emotionally bothersome, and the may mask other lesions that would otherwise be visible to mammography. Fibroadenomas are removed to alleviate pain and to alleviate the emotional burden of living with a breast lump. Even when the breast lump is confirmed to be a benign fibroadenoma, many women elect removal for these reasons. Typically, fibroadenomas are removed by lumpectomy, which is an open surgical procedure. Open surgical recision requires a fairly large incision, creates an unsightly scar on the breast and a scar inside the breast that interferes with mammography, and it requires general anesthesia.

In our prior patent, Littrup, Method and System for Cryoablating Fibroadenomas, U.S. Pat. No. 6,789,545 (Sep. 14, 2004), and Van Bladel, et al., Device For Biopsy And Treatment Of Breast Tumors, U.S. Pat. No. 6,494,844 (Dec. 17, 2002), we disclosed systems for treating fibroadenomas in the breast of female patients. In U.S. Pat. No. 6,789,545, we proposed a cryosurgical treatment regimen comprising a period of high power freezing to very low temperature, followed by a period of low power freezing, followed by a period of thawing, and a repetition of high power freezing and low power freezing, followed by thawing and/or warming of the cryoprobe. In this procedure, the cryoprobe was operated to achieve a cryogenic temperature of −150° C. during the high-power freezing period, as measured by a temperature sensor within the cryoprobe. The cryoprobe was then operated to maintain a cyrogenic temperature of −45° C. or below. This procedure has proven to be quite effective and reliable. The U.S. Food and Drug Administration currently requires that this gold standard of treatment (double freeze-thaw to the critical temperature of −40° C. within the mass) be used in the treatment of fibroadenomas.

However, our experience with fibroadenoma patients has led to the development of the new procedure described below which is faster and more efficient, but which retains the advantages of our prior method including creation of a smaller iceball fitted to the fibroadenoma, reduced ablation of healthy tissue surrounding the fibroadenoma, reduced potential for damage to the skin overlying the fibroadenoma, and reduced resorption time for the ablated mass. In our experience, we have determined that fibroadenoma regrowth is insubstantial, regardless of thaw achieved during the thaw cycle. Thus it appears that the "thaw-induced" cell death mechanism must be substantially complete upon warming of the ice ball to 0° C. (or even earlier), so that complete thawing is unnecessary. Whether the iceball thaws completely or not at all does not affect the long-term success of fibroadenoma cryoablation. Also, the cooling-induced cell death mechanism appears to be complete, for fibroadenomas and perhaps other lesions, by the time the tissue has reached −20° C. Further cooling to lower temperatures, and cooling for extended periods beyond that necessary to reach this temperature, do not appear to affect the long-term success of fibroadenoma cryoablation. Thus, though there is no reasonable expectation, based on the state of art, that the methods and systems described below would provide adequate treatment, our experience indicates that, for fibroadenoma, treatments which represent a departure from the current gold standard of cryoablation are safe and effective.

SUMMARY

The methods and systems described below provide for safe and effective cryoablation of fibroademonas with a minimally invasive cryosurgical procedure. The procedure entails use of a cryoprobe to cryoablate a fibroadenoma with a treatment regimen that takes less time and consumes less cryogen than currently accepted treatment regimens. Cryoablation is performed with a treatment regimen including two freeze cycles with an intervening passive warming period, without an intervening low-power freeze cycle. When accomplished with commercially available cryoprobes such as our Visica® argon gas cryoprobes system or our new Visica II™ liquid nitrogen cryoprobes system, the method entails a period of freezing to attain a −20° C. isotherm coincident with the boundaries of the fibroadenoma, followed by a period of passive warming, followed by a repetition of these steps, and optionally followed by a warming cycle to speed removal of the cryoprobe from the iceball.

To achieve the coincident iceball, the cryoprobes are adapted to achieve an oblong iceball (such as an ellipsoid or prolate spheroid (roughly, the shape of a rugby ball or American football) or ovoid (egg-shaped)) which roughly matches the typical shape of a target fibroadenoma. The cryoprobe tip is pushed into and through the target fibroadenoma so that its distal tip protrudes from the far boundary of the target fibroadenoma. The cryoprobes is then operated to create an iceball engulfing the fibroadenoma, such that at the margins of the fibroadenoma the temperature reaches −20° C. in a period of time which depends on the size of the fibroadenoma. (That is, the cryoprobes are operated for a period of time, which depends on the size of the fibroadenoma, necessary to create an iceball engulfing the fibroadenoma, such that at the margins of the fibroadenoma the temperature reaches about −20 C or less.) The treatment is achieved with two freezing periods, with at least one of the freezing periods achieving the −20° C. isotherm engulfing the fibroadenoma, without a higher-temperature freezing period, and with a passive warming/thawing period between the two freezing periods that is determined empirically to achieve warming sufficient to exhaust known warming cell-death mechanisms. The cryoprobe is operated to achieve an iceball with a −20° C. isotherm of the desired diameter based on empirically determined parameters. In clinical practice, it depends on the length of time a cryoprobe is operated and its duty cycle, and this in turn depends on the cooling power of the cryoprobes, the shape of the iceball, and the location of the cryoprobe tip relative to the fibroadenoma.

Performance of the method is facilitated by a control system that sets the appropriate freeze and passive warming cycle times based on operator input of the size of the fibroadenoma to be treated. The desired time for freezing fibroadenomas of various sizes is selected based on empirical experience, and is preprogrammed into the system control box. After entry of the fibroadenoma size and selection of cycle parameters, the system operates automatically to apply cooling to the fibroadenoma as desired by the surgeon. The progress of the cryosurgery may be monitored with ultrasound and thermocouples. The method may also be performed by a control system that allows a surgeon or technician to enter desired periods of freezing and the intermediate periods of passive warming time manually.

BRIEF DESCRIPTION OF THE DRAWINGS

FIG. 4 illustrates the control system interface for fibroadenoma cryoablation with predetermined cycle times.

FIG. 5 illustrates the control system interface for fibroadenoma cryoablation with predetermined cycle times, after entry of the lesion size.

DETAILED DESCRIPTION OF THE INVENTION

Figure 1:
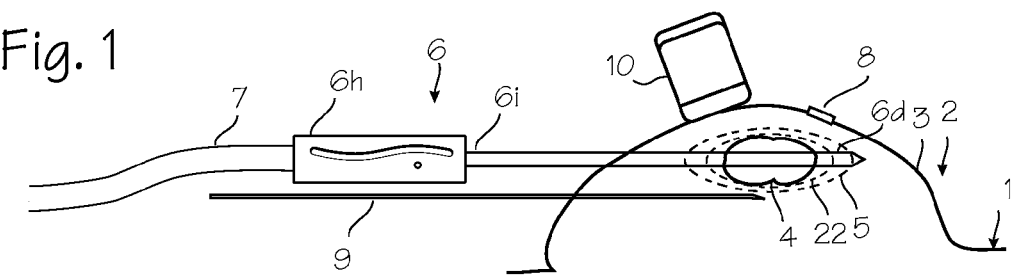
FIG. 1 illustrates the cryosurgical procedure for treating benign tumors in the breast.

FIG. 1 illustrates the cryosurgical procedure for treating benign tumors in the breast. The patient 1 and the patient's breast 2 and skin 3 of the breast are shown schematically. The fibroadenoma 4 is located within the breast, surrounded by soft tissue and fatty tissue. The fibroadenoma is a well-defined, hard mass ranging in size from 3 to 40 mm in diameter. The purpose of the procedure is to form an iceball 5 (the frozen mass of breast tissue) around the fibroadenoma, after which the natural healing processes of the body will result in resorption of the fibroadenoma by the patient's body. The iceball is formed with a cryoprobe 6, which, as illustrated, includes a handle portion 6h and an insertion portion 6i which is inserted through the skin and intervening breast tissue into the fibroadenoma, so that the distal tip extends through the fibroadenoma. A cryogen supply hose 7 is attached to the cryoprobe and serves to supply liquid cryogen or high-pressure gas to the cryoprobe. The cryoprobe may include a temperature sensor, which directly or indirectly measures the temperature of the cryoprobe. An external temperature sensor 8 may be used during the surgery to monitor skin temperature, so that surgeons can avoid causing frost-bite on the patient's skin. An internal temperature sensor 9 may be inserted into the breast to monitor the creation and maintenance of the iceball or the approximate location of the −20° C. isotherm.

Figure 2:
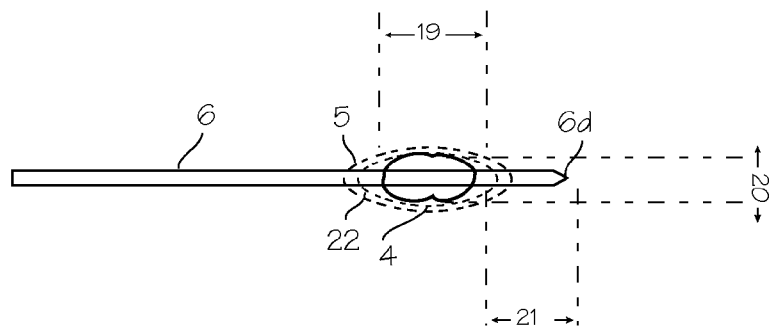
FIG. 2 illustrates the geometry of a typical fibroadenoma and the desired iceball used to ablate the fibroadenoma.

FIG. 2 illustrates the geometry of a typical fibroadenoma and the desired iceball used to ablate the fibroadenoma. The common fibroadenoma 4 is typically oblong, characterized by a major axis 19 and a minor axis 20. The fibroadenoma may range in size from less than 1 cm along the major axis to 4 cm along the major axis (less than 10% of fibroadenomas exceed 4 cm in length). The length along the major axis is typically 1.3 times the width across minor axis, so that the common fibroadenoma is oblong. To accomplish the ablation procedure with minimal overkill, the cryoprobe 6 has been designed to create an oblong iceball (such as an ellipsoid or prolate spheroid (roughly, the shape of a rugby ball or American football) or ovoid (egg-shaped)) which matches the typical shape of a target fibroadenoma. The cryoprobe is inserted into the breast (through a small incision) and pushed into the fibroadenoma mass so that the distal tip 6d protrudes past the far boundary (the distal boundary in relation to the cryoprobe) by a length 21. The length of distal protrusion 21 may be varied according the size of the fibroadenoma, to place the center of iceball near the center of the fibroadenoma. The iceball tends to form first at a known position probe, and then grow proximally and distally along the probe, but it is currently easier to visualize the distal protrusion that it is to visualize the coincidence of the probe's expected iceball and the center of the fibroadenoma. The iceball 5 is coldest at its center (at the surface of the cryoprobe). The 0° C. isotherm represents edge of the iceball (the boundary between frozen tissue and un-frozen tissue), while the −20° C. isotherm 22 lies within the iceball. The −20° C. isotherm is the boundary of that part of the iceball with is at or below −20° C. We want the volume of ice encompassed by the −20° C. isotherm to encompass the fibroadenoma. In many cases, there may be a region of healthy tissue both distal and proximal to the fibroadenoma which is encompassed within the −20° C. isotherm. This is acceptable, given that the overkill zone will heal along with ablated fibroadenoma. The overkill zones may be reduced by providing cryoprobes of various sizes to match the fibroadenomas.

The cryoprobe used for the procedure may be our Visica 2™ 3.4 mm cryoprobe (which uses liquid nitrogen), our Visica® cryoprobe (which uses argon gas and a Joule-Thomson cryostat), or other commercially available cryoprobes. Our Visica 2™ cryoprobe and system are described in detail in our prior U.S. application Ser. No. 11/318,142 filed Dec. 23, 2005 and Ser. No. 11/406,547 filed Apr. 18, 2006 (212/846) and their corresponding PCT application PCT/US06/48863 filed Dec. 22, 2006, the entirety of each being incorporated by reference. For our Visica 2™ 3.4 mm cryoprobe, the probe distal tip should protrude from the distal boundary of the mass by a distance (shown as item 21) ranging from 21-23 mm for a lesion with a major axis less than 10 mm long to 5-7 mm for a lesion with a major axis less than 40 mm long, as reflected in the table below:

| Major Axis (cm) | <1.0 | 1.0-1.5 | 1.6-2.0 | 2.1-2.5 | 2.6-3.0 | 3.1-3.5 | 3.6-4.0 |
|---|---|---|---|---|---|---|---|
| Tip Protrusion (cm) | 2.3-2.1 | 2.0-1.7 | 1.6-1.4 | 1.3-1.1 | 1.1-.9 | .9-.7 | .9-.7 |

An ultrasound probe 10 is used during the procedure to visualize the formation, growth, and melting of the iceball that is formed within the breast when the cryoprobe is energized. (The iceball is highly echogenic, so that its formation is very clearly visualized. The image of the iceball is displayed on a display screen provided with the ultrasound probe.)

The probe should be inserted on or near the major axis of the mass, and the position of the probe should be verified with ultrasound or other suitable imaging system. These dimensions must be adjusted for other cryoprobe designs such that the iceball center is co-located with the lesion center.

This method of treating fibroadenomas described below provides for fast treatment without loss of effectiveness. Once situated and positioned properly relative to the target fibroadenoma, the cryoprobe is operated for two cycles of high-power freezing, with a passive warming period interposed between the cycles and a warming period provided after the second freezing cycle, without any intervening low-power freezing periods. The periods of high-power freezing are selected depending on the size of the fibroadenoma and expected time for the cryoprobe to grow an iceball with a $-20°$ C. isotherm just large enough to encompass the entire fibroadenoma. The period of passive warming between freezing periods are limited to the period necessary to allow substantial completion of known cell-death mechanisms which occur during warming. Currently, the passive warming cycles are chosen based on the period typically used for cryoablation, but with clinical experience the time to completion of warming cell death mechanisms may prove to much shorter, and the passive warming time may be adjusted accordingly. Should the warming cell death mechanisms be completed upon warming the entire ice-ball to $0°$ C. or a lower temperature, then the passive warming period may be limited to the time necessary to do so (that is, the time to warming to $0°$ C. may be coincident with or longer than the time needed to complete warming cell death mechanisms, for some lesions and cell types). With experimentation, we have empirically determined the following freeze periods for fibroadenomas of various sizes using the liquid nitrogen cryoprobes of our Visica 2™ system:

|  | Major Axis (cm) | | | | | | |
| --- | --- | --- | --- | --- | --- | --- | --- |
|  | 0-1.0 | 1.0-1.5 | 1.6-2.0 | 2.1-2.5 | 2.6-3.0 | 3.1-3.5 | 3.5-4.0 |
| 1$^{st}$ Freeze | 1 m | 1.5 m | 2 m | 3 m | 4 m | 6 m | 8 m |
| Warm | 2 m | 6 m | 8 m | 10 m | 10 m | 10 m | 10 m |
| 2$^{nd}$ Freeze | 1 m | 1.5 m | 2 m | 3 m | 4 m | 6 m | 8 m |
| Total Time | 4 m | 9 m | 12 m | 16 m | 18 m | 22 m | 26 m |

As indicated in the table, a fibroadenoma with a major axis smaller than 1 cm is treated with two freezing cycles consisting of 1 minute of freezing (engulfing the mass in a $-20°$ C. isotherm) and without a period of low power freezing, and 2 minutes of passive warming between the freezing cycles. A fibroadenoma with a major axis of 1 to 1.5 cm diameter is treated by two cycles of freezing, each consisting of 1.5 minutes (90 seconds) of freezing, with 6 minutes of passive warming between the cycles. A fibroadenoma of 1.6 to 2.0 cm diameter is treated by two cycles consisting of 2 minutes of freezing, with 8 minutes of passive warming between the freezing cycles. A fibroadenoma with a major axis of 2.1 to 2.5 cm diameter is treated by two cycles freezing, each consisting of 3 minutes freezing, with 10 minutes of passive warming between the freezing cycles. A fibroadenoma with a major axis of 2.6 to 3.0 cm diameter is treated by two cycles or freezing, each consisting of 4 minutes freezing, with 10 minutes of passive warming between the freezing cycles. A fibroadenoma with a major axis of 3.1 to 3.5 cm diameter is treated by two cycles of freezing, each consisting of 6 minutes of freezing, with 10 minutes of passive warming between the freezing cycles. A fibroadenoma of 3.6 to 4.0 cm diameter is treated by two cycles of freezing, each consisting of 8 minutes of freezing, with 10 minutes of passive warming between the freezing cycles. Then, the probe is operated for a first period limited to the approximate time necessary to create an iceball having a $-20°$ C. isotherm substantially coincident with the minor axis of the fibroadenoma, and thereafter immediately ceasing operation of the cryoprobe for a second period limited to the approximate time necessary to passively warm the iceball to $0°$ C., and immediately thereafter operating the cryoprobe for a third period approximately equal to the first period.

Thus, the method entails operating the cryoprobe for a first cooling period to create an iceball having a $-20°$ C. isotherm defining a volume engulfing the fibroadenoma, such that the $-20°$ C. isotherm is substantially coincident with an outer margin of the fibroadenoma along an axis of the fibroadenoma (preferably matching the minor axis of the iceball to the minor axis of the fibroadenoma) and thereafter, without substantial delay, ceasing operation of the cryoprobe for a warming period limited to the time necessary to allow the iceball to warm to $0°$ C. (without thawing) and allow completion of warming cell death mechanism, and thereafter, again without substantial delay, operating the cryoprobe for a second cooling period to create an iceball having a $-20°$ C. isotherm defining a volume engulfing the fibroadenoma, such that the $-20°$ C. isotherm is substantially coincident with an outer margin of the fibroadenoma along an axis of the fibroadenoma, and thereafter, again without substantial delay, ceasing cooling operation of the cryoprobe and allowing or causing the cryoprobe to warm as necessary to remove the cryoprobe. Also, the warming necessary to remove the cryoprobe may be augmented by application of heat through the cryoprobe through any suitable active warming mechanism.

The cooling periods are preferably predetermined, in the sense that they are determined empirically based on the typical time required to create an iceball having a $-20°$ C. isotherm defining a volume engulfing a typical fibroadenoma of the same approximate size as the fibroadenoma to be treated with a cryoprobe of similar design to the cryoprobe used to treat the fibroadenoma. The second cooling period may be determined empirically, based on the typical time required to create an iceball having a $-20°$ C. isotherm defining a volume engulfing a typical fibroadenoma of the same approximate size as the fibroadenoma to be treated (in which case it is equivalent to the first cooling period), or based on the typical time required to cool the warmed iceball to re-create an iceball having a $-20°$ C. isotherm (in which case it may be substantially shorter than the first cooling period, because it starts from a frozen state). Because cryoprobes of different design have different efficiencies and cooling powers, the predetermined cycle times may vary with the design of the cryoprobe and the operating mode of the cryoprobe.

This algorithm for treatment is sufficient for treating fibroadenomas up to 4 cm. Larger fibroadenomas, which are uncommon, may require additional procedures. A warming cycle of 30 to 60 seconds, with the primary goal of releasing the probe from the iceball, may be performed after the second freezing cycle to speed release of the cryoprobe from the iceball.

These time periods may be varied to accomplish other regimens falling under the general description of two freezing cycles comprising creation of an iceball having a $-20°$ C. isotherm substantially engulfing or coincident with the fibroadenoma, with a warming period between the freezing cycles. It is specifically contemplated that they be adjusted to account for cryoprobes of differing cooling power or cryoprobes from different manufacturers, and that the fibroadenoma size ranges be condensed or expanded as clinical experience dictates.

Figure 3:
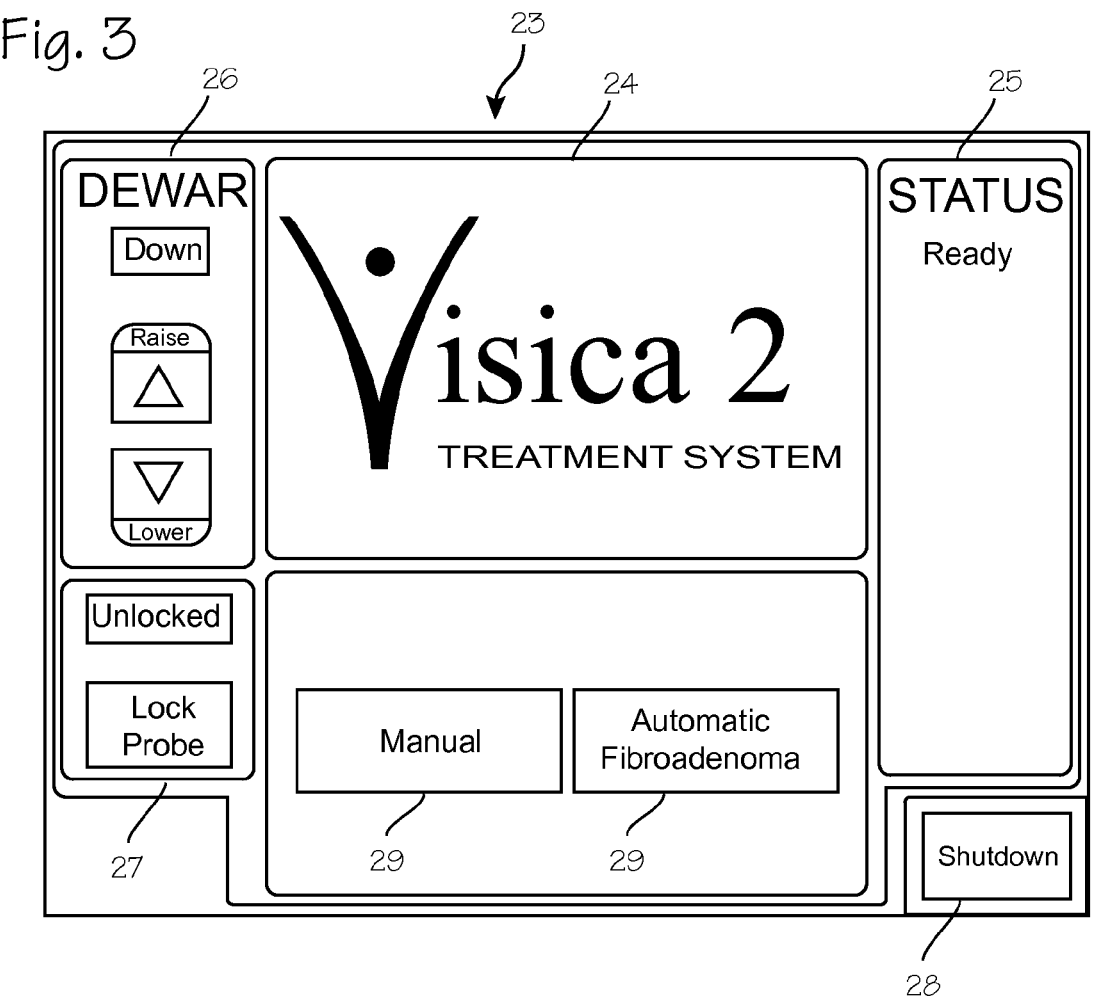
FIG. 3 illustrates the interface for controlling a cryoprobe to accomplish the cryoablation of a fibroadenoma.

FIG. 3 illustrates a control system designed to implement the method described above. The control system is described in reference to our Visica 2™ cryoablation system which uses low pressure liquid nitrogen as the cryogen. The control system is currently implemented in Windows compatible software running and can be run on any suitable hardware platform. FIG. 3 shows an initial screen shot 23, presented to the operator upon system startup. This screen includes a splash screen 24, a status window 25 for presenting various messages to the use, a dewar status/control window 26, a cryoprobe status/control window 27, and a shutdown command window 28, and mode selection buttons 29 and 30. The splash screen is used to identify the software module to the operator. The status window is used to provide output indicative of the status of the system, including various messages that can guide the operator in the use of the system, advise the operator of any system faults, etc. The dewar status/control window is used to indicate the position of the dewar, which in the underlying hardware system is a small flask which is lifted into a secure connection with a the cryoprobe interconnection. This window also includes the touch screen buttons for raising and lowering the dewar. The cryoprobe status/control window is used to indicate that status of the cryoprobe connection to the cryoprobe interconnection, and also includes touch screen buttons for locking the cryoprobe supply hose into place in the dewar opening. The mode selection buttons are used to select the mode of operation desired by the operator.

Figure 6:
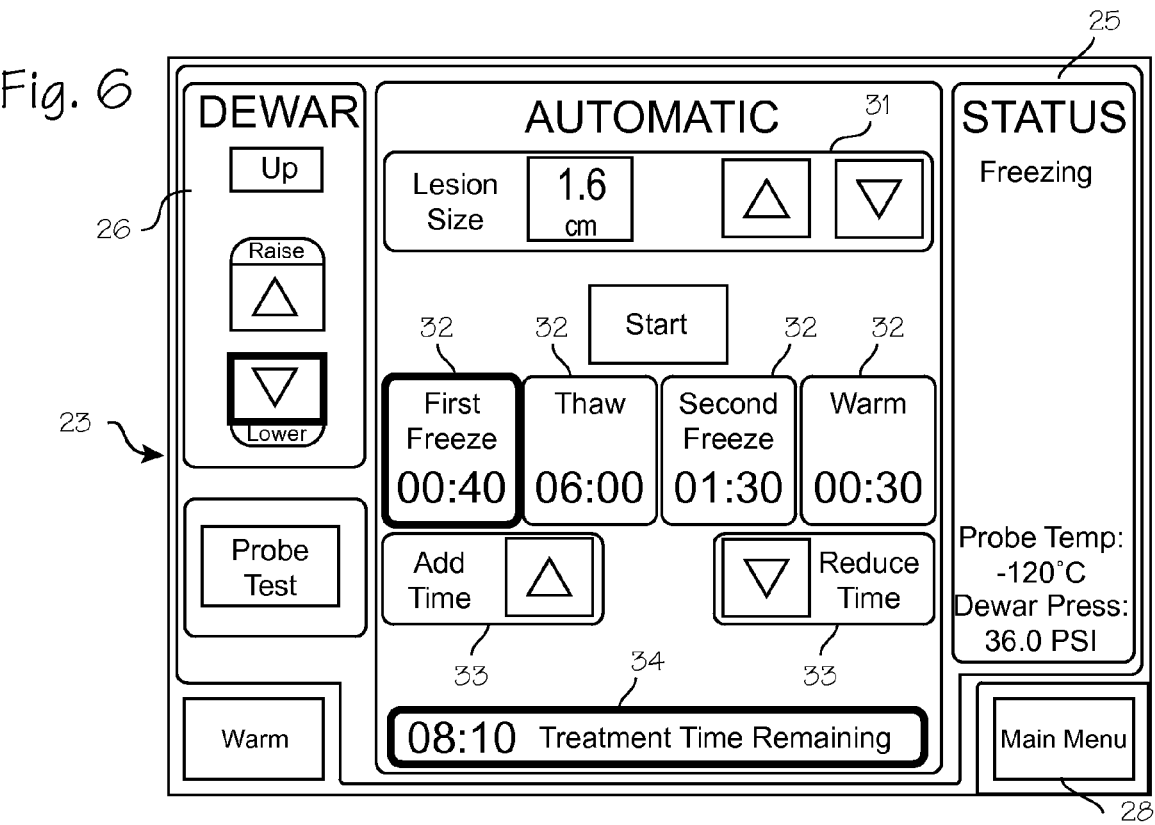
FIG. 6 illustrates the control system interface for fibroadenoma cryoablation with predetermined cycle times, during a freeze cycle.

FIGS. 4, 5 and 6 illustrate the control system interface for fibroadenoma cryoablation with predetermined cycle times. The main window of this screen provides a lesion size selector window 31 for entry of the lesion size (as determined by the operator using any suitable visualization technique). The lesion size used here is the measured long axis, or major axis, of the fibroadenoma. The cycle time windows 32 are filled by the control system with values determined from the table above. In that sense, the system is automatic, as the cycle times are chosen by the system without further input from the operator. A table reflecting the desired predetermined cycle times for fibroadenomas of various sizes is stored in the control system memory, and the control system is programmed to look up and enter predetermined cycle times matching the operator inputted fibroadenoma size, and then control the cryoprobe and cryogen fluid system to accomplished the desired regimen.

The cycle times are shown in FIG. 5, which reflects that the operator has entered a lesion size of 1.6 cm, and the control system has entered freeze times of 1 minute 30 seconds, and a "Thaw" time of 6 minutes (the term "THAW" is used in the control screen to distinguish it from the "WARM" button used for active warming, and because operators will equate the passive warming cycle with the old-style warming cycle, notwithstanding the fact that the intention is to warm the iceball without wasting time waiting for it to thaw), and a warm time of 30 seconds. The operator can override these automatically entered values using the adjustment buttons 33 to either increase or decrease the cycle times to account for any unusual conditions. The countdown window 34 indicates the total procedure time remaining. Other buttons provided in this interface window are the main menu selection button, for returning to the main menu, and the probe test button, for initiating a test of the probe prior to the procedure, and a "warm" button initiate warming immediately (and also stop cryogen flow) should a procedure need to be terminated and the probe withdrawn without delay.

FIG. 6 illustrates the control system interface for fibroadenoma cryoablation with predetermined cycle times, after the freezing operation has begun. The control system provides output via the display by highlighting the window for the current cycle time (in this case, the first freeze), and by displaying a countdown of time remaining in countdown window 34. In this case, the first freeze cycle has been underway for fifty seconds, so that the system indicates forty seconds remaining for the first freeze cycle and 8 minutes and ten seconds remaining for the entire procedure. As the control system controls the fluid system to provide the passive warming cycle (labeled "THAW" in the figure), the second freeze cycle, and the active warming cycle, the control system will operate the interface to highlight the corresponding cycle time window.

Figure 7:
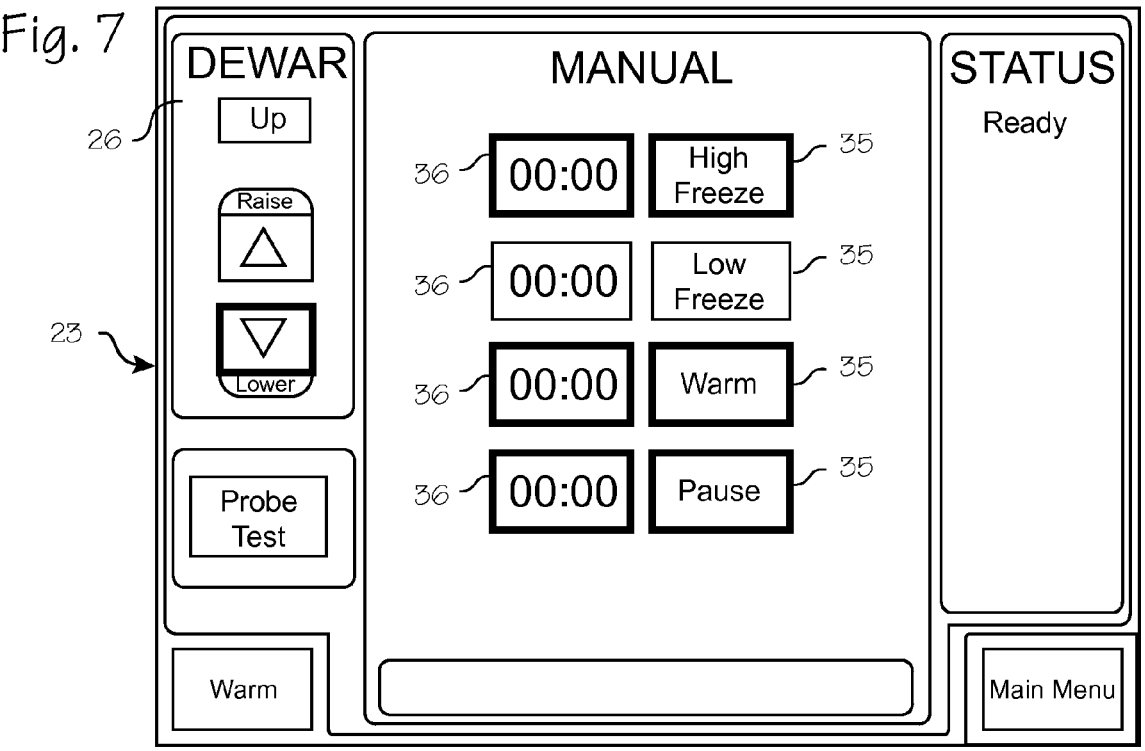
FIG. 7 illustrates the control system interface for fibroadenoma cryoablation with operator controlled cycle times.

FIG. 7 illustrates the control system interface for fibroadenoma cryoablation with operator controlled cycle times. This window provides several cycle selection buttons 35 and associates timer windows 36. In this mode, the operator starts each cycle by selecting the desired cycle selection button and merely monitors the cycle time, and selects another cycle when, in the operator's discretion, the desired time in cycle has been achieved. In this window, a "low freeze" selector button is retained in case the operator wants to use the system for other procedures, such as cryo-assisted lumpectomy or traditional double freeze-thaw cryosurgical ablation.

Figure 8:
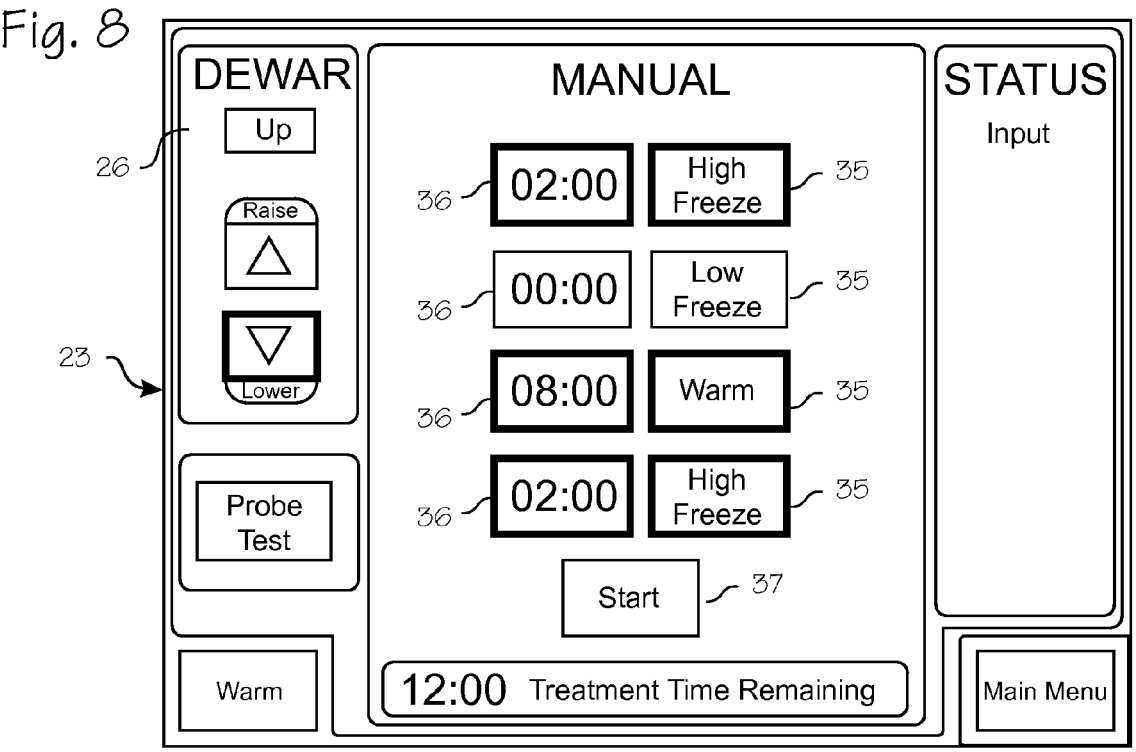
FIG. 8 illustrates the control system interface for fibroadenoma cryoablation with manually entered cycle times.

FIGS. 8 illustrates the control system interface for fibroadenoma cryoablation with operator-inputted cycle times. As cycle time selector button 35 is selected, the system will present the operator with interface elements for inputting the desired time, which will then appear in the associated timer windows 36. When the control system has received operator-entered times for each cycle, the control system will enable the start button 37, whereupon the operator may select the start button to initiate the procedure. In response to this signal to initiate the procedure, the control system will control the appropriate hardware to apply cryogen to the cryoprobe as necessary to perform freezing and warming for the operator-entered time periods, and also operate the warming mechanisms to achieved the operator-entered warm cycle. The control system will also display the procedure time remaining in the countdown window.

The system illustrated in FIGS. 7 and 8 allow for manual performance of the method. This may be accomplished using empirically determined time periods, as described for the systems which automatically input empirically predetermined cycle times, or it may be accomplished in situ using feedback from the separately place temperature sensor (item 9 in FIG. 1). In this case, the first cooling period is determined in situ, by placing the temperature probe proximate the outer margin of the fibroadenoma and operating the cryoprobe during the first cooling period until the temperature at the temperature probe reaches $-20°$ C. The second cooling period may be determined in situ, using the temperature probe proximate the outer margin of the fibroadenoma and operating the cryoprobe during the second cooling period until the temperature at the temperature probe reaches $-20°$ C., or the operator can assume that the second cooling period should be the same as the first cooling period, and apply cooling in the second period for the same time as that applied in the first cooling period. The warming period may also be determined in situ, and is determined by the time required for temperature at the separately place temperature probe to reach $0°$ C., or by the time required for temperature of the cryoprobe, as measured in a region of the cryoprobe within the iceball, to reach $0°$ C.

The control system described in reference to FIGS. 3 through 8 is designed to use touch screen inputs or mouse inputs as the primary operator input. Thus, the control system is programmed to indicate, with suitable visual prompts (highlighting graphical elements with background colors, bouncing graphical elements, enlarging fonts, dimming screen elements, etc.) active screen elements, screen windows that require data entry, and other interface information.

The system is implemented through a control system (a computer, microprocessor, or other control circuit) and appropriate displays and operator input devices necessary to accept operator input, along with the solenoid operated valves operably connected to the control system such that the control system can control the cryogen flow to the cryoprobe according to the operator's input. For liquid nitrogen embodiments of the system, the system is connected to a pressurized source of liquid cryogen or provides for interconnection between the cryoprobe and a pressurized source of liquid cryogen. For gas cryoprobe embodiments of the system, the control box includes gas connections for connecting the gas supply hose to a valve inside the box which controls cooling gas supply to the cryoprobe. Various valves and electromechanical controls within the control box comprise a fluid supply assembly which serves to operably connect the cryoprobe to a cooling fluid source and, optionally, to a warming fluid source. The cooling fluid is preferably high-pressure argon gas, and the warming fluid is preferably high-pressure helium gas.

Figure 9:
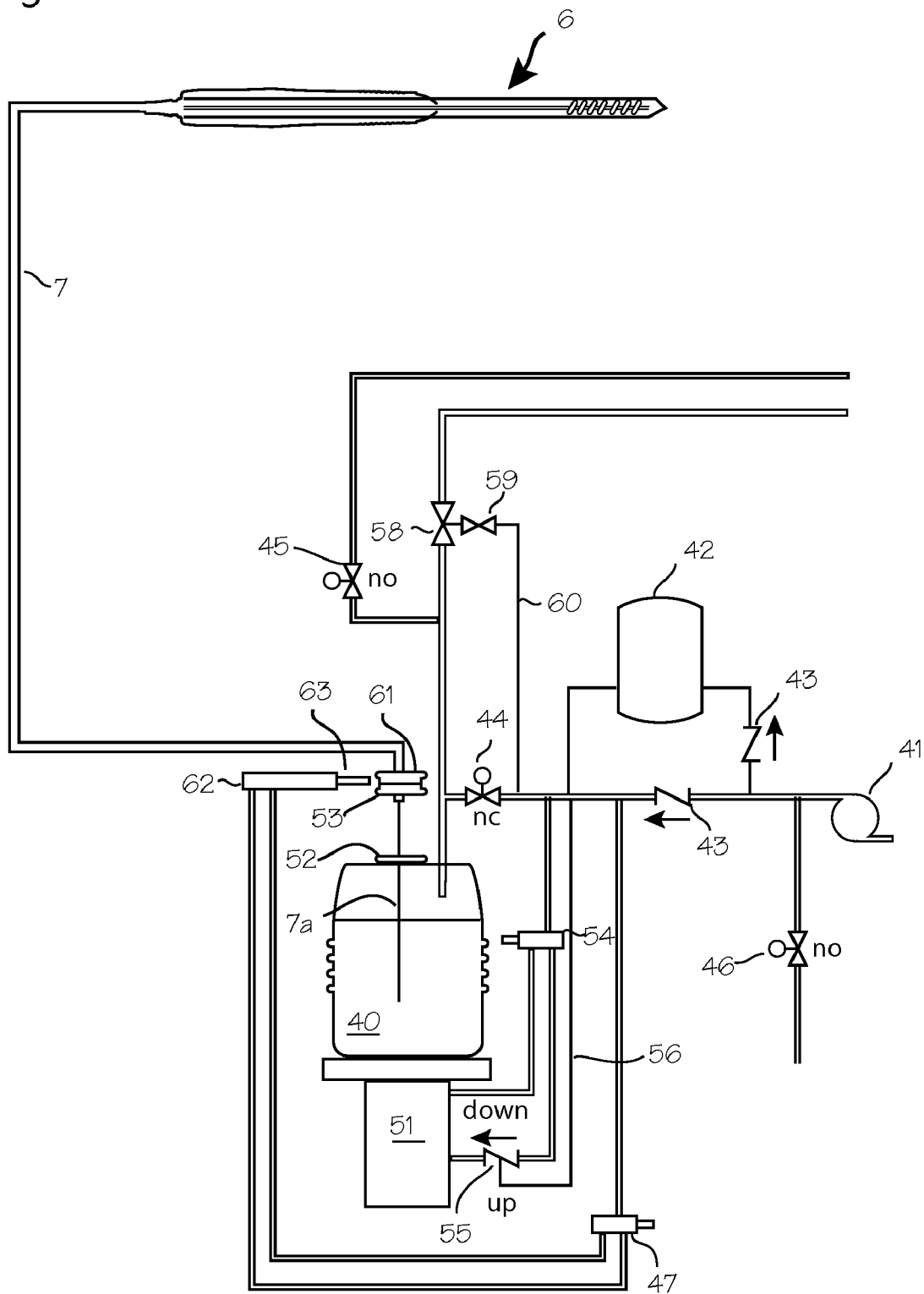
FIG. 9 illustrates a suitable cryogen fluid system for the cryoprobe.

FIG. 9 illustrates a suitable cryogen fluid system for the cryoprobe. The cryosurgical system comprises the cryoprobe 6, the supply hose 7 and cryogen supply tube 7a (which runs uninterrupted, within the supply hose, from the dewar to the probe), a cryogen source dewar 40, pressurization pump 41. The desired flow of cryogen from the cryogen source to the cryoprobe is induced in this embodiment by pressurizing the cryogen source with air delivered by the pressurization pump. In this system, the cryogen is supplied in a simple 2 liter (or 2 quart) vacuum-insulated bottle filled with liquid nitrogen (which holds enough liquid nitrogen for numerous procedures), and the pressurization pump is a simple air pump. An accumulator 42 is disposed in parallel between the pressurization pump 41 and the dewar 40. Check valves 43 prevent backflow from the accumulator to the pump, and pressure supply valve 44 control flows from either the accumulator or the pump into the dewar as directed by the control system. The pressure supply valve is preferably a solenoid-operated shut-off valve, which is normally closed, but opens when energized to port the output of the pressure pump and accumulator into the dewar, so that pressurized air is continuously pumped into the dewar during operation. In normal cryoprobe operation, this valve is maintained open at all times. (If desired, this valve may be replaced with a throttle valve to be operated to control pressure on the dewar, but this may increase material requirements of the pressure pump.) To control pressure in the dewar, the dewar control valve 45 is operated to bleed pressure off the top of the dewar. Dewar control valve 45 is a normally open shut-off valve, and is held shut until the dewar pressure reaches a desired initial pressure and thereafter operated to maintain predetermined steady state operating pressure, by opening and closing the valve at set points just above and below the desired average dewar pressure to maintain the pressure in a predetermined range, or about a predetermined set point. (The dewar control valve can also be provided as a throttle valve operated to maintain pressure in the dewar in the desired range, or pressure relief valve or pressure regulator set to maintain pressure in the dewar in the desired range.) This arrangement allows the system to be operated with continuous operation of the pump, without the need for a control valve coupled between the pressure source and the liquid dewar for controlling the pressure supplied to the dewar. An additional solenoid operated valve 46 is provided at the outlet of the pump, and is operated by the control system to vent the pump outlet prior to pump startup. This reduces the material requirements of the pump, allowing use of low power pump that may have difficulty starting against a high pressure head. In operation, the control system closes this valve after a short time delay after the pump starts. Each time the pump is stopped, this valve is opened by the control system to vent the pump outlet prior to the next pump start.

The control system is programmed to operate the fluid system to achieve the cryogen flow desired by the operator according the method described above. Cryogen flow is initiated when the control system causes the pump and various valves to provide pressure to the dewar. The various components may operated to pressurize the dewar to a single set pressure of about 1.5 to 2 bar (about 22 to 30 psi). To provide prompt cooldown of the cryoprobe and speed iceball growth, the fluid system may be operated to provide a slightly higher initial dewar pressure of about 2.75 to 3.5 bar (about 40 to 50 psi), and thereafter reduce the dewar pressure to a lower steady state operating pressure of 1.5 to 2 bar (about 22 to 30 psi). For example, the fluid system can be operated to pressurize the dewar to 40 psi for about 20 seconds, and then slowly reduce the pressure in the dewar to about 30 psi (over a period of about 40 seconds) by bleeding off pressure from the dewar through the dewar control valve and the cryoprobe, and thereafter maintain the pressure in the dewar at about 30 psi. Steady state pressure may be maintained by opening the dewar control valve when pressure in the dewar reaches about 32 psi, and closing the dewar control valve when the pressure in the dewar drops to about 28 psi, while operating the pressure pump continuously.

To assist the operator in installing dewars, a hydraulic lifter 51 is provided. The lifter functions to lift the dewar into position so that the dewar lip 52 is sealed in the dewar/cryoprobe interconnect fitting 53 (which is fixed in the top of a cabinet which houses the dewar. This lifter is powered by the pressurization pump in conjunction with the four-way valve 54 and the control system described above. The pneumatically operated check valve 55 is a configuration of valves that function to port pressurized air to the hydraulic lifter 51 to raise the lifter and the dewar into the position on command, lift the lifter and dewar upon loss of pressure and upon loss of system power, in order to ensure that the dewar will not remain in the lowered position or remain in a lowered position, and thus open to atmosphere, in the event of a malfunction. The pneumatically operated check valve is maintained open in both directions while pressure is maintained in sensing line 56 (which senses pressure at the pressure source), but operates as check valve when pressure is lost in the sensing line. This configuration of valves operates such that, if power is inadvertently lost during system operation, the lifter valve (which is normally open to the UP outlet) shifts or remains aligned to the lift side of the lifter actuator, and the pneumatically operated check valve remains open, while the pump and accumulator pressure bleed off into the lifter, thereby lifting the dewar, and when the pump and accumulator pressure bleed off sufficiently, the pneumatically operated check valve pneumatically locks the lifter in the up position. (Equivalent arrangements with a pneumatically operated check valve on the down side of the accumulator can be used). Locking the accumulator in the up position prevents the dewar from freely boiling off to atmosphere, and prevents immediate decompression of the pressurized dewar. At the same time, the dewar control valve 45 (which is normally open) and the dewar dump valve 58 (which is normally open, and closes when the dump pilot valve 59 loses pressure in sensing line 60) both open, so that the dewar is quickly depressurized. The dewar dump valve and the conduit in which is it is located provide a second fluid pathway communicating from the volume of pressurized gas in the dewar to atmosphere, and this fluid pathway is sufficiently large to vent the pressure in the dewar within a short time from of 1 to 5 seconds. The avoids a dangerous expulsion of gas should the dewar overheat, or should an operator physically remove the dewar after shutdown. Also on loss of power to the system, the pressure control valve 44 closes and valve 46 opens, so the any residual pump pressure is vented to atmosphere rather than into the dewar or accumulator.

To lock the cryoprobe proximal fitting 61 into place in the probe/dewar interconnect fitting 62, a pneumatically operated locking pin 63 is provided, and is operated by pressure from the pressurization pump. In use, the dewar is raised hydraulically by the system into sealing alignment with the interconnect, and the cryoprobe proximal fitting is manually inserted into the interconnect. The interlock is then operated by the system, upon user input indicating that the cryoprobe is in place. Appropriate position sensors are used to ensure that the interlock is in place prior to operation. The system is programmed such that it requires confirmation that the locking pin is engaged in the proximal fitting prior to pressurization of the dewar.

Though the methods and systems described above have been described in the context of fibroadenoma treatment, they may also be used to treat other masses and benign or cancerous tumors in the breast, malignant neoplasia or benign dysplasia of the female genitalia, and other tumors and lesions. While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of treating a fibroadenoma in the breast of a patient, said method comprising:

inserting a cryoprobe into the fibroadenoma;

operating the cryoprobe for a first cooling period to create an iceball having a −20° C. isotherm defining a volume engulfing the fibroadenoma, said −20° C. isotherm being substantially coincident with an outer margin of the fibroadenoma along an axis of the fibroadenoma;

thereafter, without substantial delay, ceasing operation of the cryoprobe for a warming period limited to the time necessary to allow the iceball within the −20° C. isotherm to warm to 0° C. without thawing and allow substantial completion of warming cell death mechanisms;

thereafter, without substantial delay, operating the cryoprobe for a second cooling period to create an iceball having a −20° C. isotherm defining a volume engulfing the fibroadenoma, said −20° C. isotherm being substantially coincident with an outer margin of the fibroadenoma along an axis of the fibroadenoma;

thereafter, without substantial delay, ceasing cooling operation of the cryoprobe and allowing or causing the cryoprobe to warm, and removing the cryoprobe from the fibroadenoma.

2. The method of claim 1 wherein, in the step of operating the cryoprobe for a first cooling period, the first cooling period is determined empirically, based on the typical time required to create an iceball having a −20° C. isotherm defining a volume engulfing a typical fibroadenoma of the same approximate size as the fibroadenoma to be treated with a cryoprobe of similar design to the cryoprobe used to treat the fibroadenoma.

3. The method of claim 1 wherein, in the step of operating the cryoprobe for a second cooling period, the second cooling period is determined empirically, based on the typical time required to create an iceball having a −20° C. isotherm defining a volume engulfing a typical fibroadenoma of the same approximate size as the fibroadenoma to be treated with a cryoprobe of similar design to the cryoprobe used to treat the fibroadenoma.

4. The method of claim 1 wherein, in the step of operating the cryoprobe for a second cooling period, the second cooling period is determined empirically, based on the typical time required to cool the warmed iceball to re-create an iceball having a −20° C. isotherm defining a volume engulfing a typical fibroadenoma of the same approximate size as the fibroadenoma to be treated with a cryoprobe of similar design to the cryoprobe used to treat the fibroadenoma.

5. The method of claim 1 wherein, in the step of operating the cryoprobe for a second cooling period, the second cooling period is operated for a period equivalent to the first cooling period.

6. The method of claim 1 wherein the warming period is determined empirically, based on the typical time required to warm an iceball of the size created in the first cooling period, within the body, to 0° C. without thawing the iceball, and to permit a substantial degree of warming cell-death mechanism to Occur.

7. The method of claim 1 wherein, in the step of operating the cryoprobe for a first cooling period, the first cooling period is determined in situ, by placing a temperature probe proximate the outer margin of the fibroadenoma and operating the cryoprobe during the first cooling period until the temperature at the temperature probe reaches −20° C.

8. The method of claim 7 wherein, in the step of operating the cryoprobe for the second cooling period, the second cooling period is determined in situ, by placing a temperature probe proximate the outer margin of the fibroadenoma and operating the cryoprobe during the second cooling period until the temperature at the temperature probe reaches −20° C.

9. The method of claim 7 wherein, in the step of operating the cryoprobe for the second cooling period, the second cooling period is equivalent to the first cooling period.

10. The method of claim 7 wherein, n the warming period is determined in situ, and is approximated by the time required for temperature at the temperature probe to reach 0° C.

11. The method of claim 7 wherein, in the warming period is determined in situ, and is approximated by the time required for temperature of the cryoprobe, as measured in a region of the cryoprobe within the iceball, to reach 0° C.

12. A method of treating a fibroadenoma in the breast of a patient, said method comprising:

providing a cryoprobe to treat the fibroadenoma, said cryoprobe characterized by a distal end and a proximal end and a longitudinal axis, said distal end adapted for insertion into the fibroadenoma, said cryoprobe being operable to create an oblong iceball;

determining the major axis and minor axis of a fibroadenoma to be treated, and inserting the distal end of the cryoprobe into said fibroadenoma such that the longitudinal axis is substantially aligned with said major axis;

operating the cryoprobe for a first cooling period limited to the approximate time necessary to create an iceball having a −20° C. isotherm having a volume with a minor axis substantially coincident with the minor axis of the fibroadenoma, and thereafter immediately ceasing operation of the cryoprobe for a warming period limited to the approximate time necessary to passively warm the iceball within the −20° C. isotherm to 0° C. without thawing and allow substantial completion of warming cell death mechanisms, and immediately thereafter operating the cryoprobe for a second cooling period and thereafter immediately ceasing cooling operation of the cryoprobe;

withdrawing the cryoprobe from the fibroadenoma.

13. The method of claim 12 wherein, in the step of operating the cryoprobe for a first cooling period, the first cooling period is determined empirically, based on the typical time required to create an iceball having a −20° C. isotherm defining a volume engulfing a typical fibroadenoma of the same approximate size as the fibroadenoma to be treated with a cryoprobe of similar design to the cryoprobe used to treat the fibroadenoma.

14. The method of claim 12 wherein, in the step of operating the cryoprobe for a second cooling period, the second cooling period is determined empirically, based on the typical time required to create an iceball having a −20° C. isotherm defining a volume engulfing a typical fibroadenoma of the same approximate size as the fibroadenoma to be treated with a cryoprobe of similar design to the cryoprobe used to treat the fibroadenoma.

15. The method of claim 12 wherein, in the step of operating the cryoprobe for a second cooling period, the second cooling period is determined empirically, based on the typical time required to cool the warmed iceball to re-create an iceball having a −20° C. isotherm defining a volume engulfing a typical fibroadenoma of the same approximate size as the fibroadenoma to be treated with a cryoprobe of similar design to the cryoprobe used to treat the fibroadenoma.

16. The method of claim 12 wherein, in the step of operating the cryoprobe for a second cooling period, the second cooling period is operated for a period equivalent to the first cooling period.

17. The method of claim 12 wherein the warming period is determined empirically, based on the typical time required to warm an iceball of the size created in the first cooling period, within the body, to 0° C. without thawing the iceball.

18. The method of claim 12 further comprising:
determining the major axis of the fibroadenoma;
for fibroadenomas having a major axis of 1 cm or less, operating the cryoprobe to create the iceball for a period of 1 minute, then allowing the iceball to warm for a period of 2 minutes, then, operating the cryoprobe to create the iceball for a period of 1 minute;
for fibroadenomas having a major axis of 1.0 to 1.5 cm, operating the cryoprobe to create the iceball for a period of 1.5 minutes, then allowing the iceball to warm for a period of 6 minutes, then operating the cryoprobe to create the iceball for a period of 1.5 minutes;
for fibroadenomas having a major axis of 1.5 to 2.0 cm, operating the cryoprobe to create the iceball for a period of 2 minutes, then allowing the iceball to warm for a period of 8 minutes, then operating the cryoprobe to create the iceball for a period of 2 minutes;
for fibroadenomas having a major axis of 2.1 to 2.5 cm, operating the cryoprobe to create the iceball for a period of 3 minutes, then allowing the iceball to warm for a period of 10 minutes, then operating the cryoprobe to create the iceball for a period of 3 minutes;
for fibroadenomas having a major axis of 2.6 to 3.0 cm, operating the cryoprobe to create the iceball for a period of 4 minutes, then allowing the iceball to warm for a period of 10 minutes, then operating the cryoprobe to create the iceball for a period of 4 minutes;
for fibroadenomas having a major axis of 3.1 to 3.5 cm, operating the cryoprobe to create the iceball for a period of 6 minutes, then allowing the iceball to warm for a period of 10 minutes, then operating the cryoprobe to create the iceball for a period of 6 minutes;
for fibroadenomas having a major axis of 3.6 to 4.0 cm, operating the cryoprobe to create the iceball for a period of 8 minutes, then allowing the iceball to warm for a period of 10 minutes, then operating the cryoprobe to create the iceball for a period of 8 minutes;

withdrawing the cryoprobe from the fibroadenoma.

19. A system for treating fibroadenoma in the breast of a patient, said system comprising:
a cryoprobe, said cryoprobe characterized by a distal end and a proximal end and a longitudinal axis, said distal end adapted for insertion into the fibroadenoma, said cryoprobe being operable to create an iceball;
a cryogen fluid system operable to control the cryoprobe to cool the distal tip of the cryoprobe to cryogenic temperatures;
a control system of controlling the cryogen fluid system and cryoprobe to selectively cooled the cryoprobe
said control system programmed to accept input from a user regarding the size of a fibroadenoma to be treated, and thereafter operate the cryoprobe and cryogen fluid system to provide cooling to the cryoprobe;
said control system further programmed to operate the cryoprobe and cryogen fluid system to operate the cryoprobe for a first cooling period, followed immediately by a warming period, followed immediately by a second cooling period;
said control system programmed to operate the cryoprobe for predetermined cooling and warming periods, said predetermined cooling and warming periods depending on the size of the fibroadenoma as inputted by the user, said cooling and warming periods being predetermined as follows:
for a first cooling period, to a time limited to the approximate time necessary to create an iceball having a −20° C. isotherm substantially coincident with an axis of the target fibroadenoma;
for a warming period, to a time limited to the approximate time necessary to passively warm the iceball within the −20° C. isotherm to 0° C. and allow substantial completion of warming cell death mechanisms;
for a second cooling period, to a time limited to the approximate time necessary to create an iceball having a −20° C. isotherm substantially coincident with an axis of the target fibroadenoma.

20. The system of claim 19 wherein the predetermined cooling and warming periods are inputted into the control system and correlated to potential user-inputted fibroadenoma sizes as follow:
for fibroadenomas having a major axis of 1 cm or less, operating the cryoprobe to create the iceball for a period of 1 minute, then allowing the iceball to warm for a period of 2 minutes, then, operating the cryoprobe to create the iceball for a period of 1 minute;
for fibroademonas having a major axis of 1.0 to 1.5 cm, operating the cryoprobe to create the iceball for a period of 1.5 minutes, then allowing the iceball to warm for a period of 6 minutes, then operating the cryoprobe to create the iceball for a period of 1.5 minutes;
for fibroademonas having a major axis of 1.5 to 2.0 cm, operating the cryoprobe to create the iceball for a period of 2 minutes, then allowing the iceball to warm for a period of 8 minutes, then operating the cryoprobe to create the iceball for a period of 2 minutes;

for fibroademonas having a major axis of 2.1 to 2.5 cm, operating the cryoprobe to create the iceball for a period of 3 minutes, then allowing the iceball to warm for a period of 10 minutes, then operating the cryoprobe to create the iceball for a period of 3 minutes;

for fibroademonas having a major axis of 2.6 to 3.0 cm, operating the cryoprobe to create the iceball for a period of 4 minutes, then allowing the iceball to warm for a period of 10 minutes, then operating the cryoprobe to create the iceball for a period of 4 minutes;

for fibroademonas having a major axis of 3.1 to 3.5 cm, operating the cryoprobe to create the iceball for a period of 6 minutes, then allowing the iceball to warm for a period of 10 minutes, then operating the cryoprobe to create the iceball for a period of 6 minutes;

for fibroademonas having a major axis of 3.6 to 4.0 cm, operating the cryoprobe to create the iceball for a period of 8 minutes, then allowing the iceball to warm for a period of 10 minutes, then operating the cryoprobe to create the iceball for a period of 8 minutes.

* * * * *